United States Patent [19]

Lampe et al.

[11] Patent Number: 5,756,663

[45] Date of Patent: May 26, 1998

[54] **ANTIARRHYTHMIC PEPTIDE FROM VENOM OF SPIDER *GRAMMOSTOLA SPATULATA***

[75] Inventors: Richard Alexander Lampe, Pennsville, N.J.; Frederick Sachs, Eden, N.Y.

[73] Assignee: Zeneca Limited, London, England

[21] Appl. No.: 775,477

[22] Filed: Dec. 30, 1996

Related U.S. Application Data

[60] Provisional application No. 60/009,580 Jan. 3, 1996.

[51] Int. Cl.$^6$ .................... A61K 38/16; C07K 14/00
[52] U.S. Cl. .................... 530/324; 514/2; 514/12
[58] Field of Search .................... 530/324; 514/12

[56] References Cited

U.S. PATENT DOCUMENTS

| | | | |
|---|---|---|---|
| 4,925,664 | 5/1990 | Jackson et al. | 424/537 |
| 5,064,657 | 11/1991 | Jackson et al. | 424/537 |
| 5,122,596 | 6/1992 | Phillips et al. | 530/350 |
| 5,196,204 | 3/1993 | Jackson et al. | 424/538 |
| 5,281,693 | 1/1994 | Jackson et al. | 530/324 |

OTHER PUBLICATIONS

Lampe et al., 'Isolation and Pharmacological Characterization of ω–Grammotoxin SIA, a Novel Peptide inhibitor of Neuronal Voltage–Sensistive Calcium Channel Responses', Molecular Pharmacology, 44:451–460, Mar. 18, 1993.

*Primary Examiner*—Cecilia J. Tsang
*Assistant Examiner*—Michael L. Borin
*Attorney, Agent, or Firm*—Liza D. Hohenschutz

[57] ABSTRACT

The invention provides a novel peptide isolated from the venom of the spider *Grammostola spatulata* which peptide has antiarrhthymic activity. The invention also provides methods of treating arrhthymia comprising administering to a patient in need of such treatment an effective amount of the peptide. The invention further provides pharmaceutical compositions and methods of mediating hypotonic cell swelling induced calcium increase in cells.

3 Claims, No Drawings

ANTIARRHYTHMIC PEPTIDE FROM VENOM OF SPIDER GRAMMOSTOLA SPATULATA

This application claims the benefit of U.S. Provisional Application No. 60/009,580 filed on Jan. 3, 1996.

FIELD OF THE INVENTION

The present invention relates to the field of peptides having stretch-activated channel activity. More particularly the present invention relates to peptides obtainable from venom of *Grammostola spatulata*, the Chilean pink tarantula spider, that are capable of blocking stretch-activated channels and have antiarrhythmic activity.

BACKGROUND OF THE INVENTION

Mechanosensitive ion channels (MCSs) were discovered in tissue cultured skeletal muscle cells using single channel patch clamp recording and have since been found in both the plant and animal kingdoms and in the cells of most tissues. Most of them open with increasing membrane tension [stretch-activated channels (SACs)], but a few are tonically active and close with increasing tension [stretch-inactivated channels (SICs)]. In at least one case, the channels are also sensitive to the sign of the patch curvature. In animal cells, the channels tend to display selectivity for either generic cations or potassium. MSCs form a family that is generally distinct from known channels families, i.e. most channels are not mechanically sensitive.

Ion selectivity of the MSC channel family is variable, as in the case of voltage-activated or ligand-activated channel families. In the animal cells, the most common forms are cation selective and, more particularly, potassium selective. The cation channels will pass divalents such as $Ca^{+2}$ and $Ba^{+2}$ as well as monovalents. Due to their ability to pass $Ca^{+2}$, effects of cationic MSCs are potentially complicated. Even under voltage clamp conditions, incoming $Ca^{+2}$ may activate other channels, such as $Ca^{2+}$activated $Cl^-$channels, a link that has been invoked in the regulation of cell volume.

Investigations of spider venoms for identification of biological entities with commercial potential has focused primarily on the agrochemical sector. The ultimate goal of these activities has been the search for chemical constituents which interact selectively with invertebrate species to induce paralysis or death with minimal mammalian toxicological properties. However in recent years, spider venoms have joined the other predator-derived venoms being exploited for identification of compounds which identify mammalian targets and which assist the development of pharmaceuticals. The arachnid species *Grammostola spatulata*, commonly referred to as the Chilean pink tarantula spider, is a member of the Theraphosidae family and the Chelicerata order. Previous studies by Lampe et al. (1993) Molecular Pharmacology 4:451–460 showed that venom of *G. spatulata* contains a peptide which interacts in a non-selective manner with voltage-sensitive calcium channels.

Ventricular fibrillation is a frequent cause of sudden death in the United States and Europe. It has been suggested that abnormal mechanical factors induce electrophysical changes conducive to arrhythmia via "mechanoelectric feedback". Sarcolemma stretch-activated channels have been postulated as a mechanism of mechanoelectric feedback and they may play a role in the genesis of stretch-activated arrhthymias.

SUMMARY OF THE INVENTION

The present invention provides a novel purifiedpeptide obtainable from the venom of the pink Chilean tarantula spider, Grammostola spatulata. The peptide (referred to hereinafter as a mechanotoxin or GsAF II) is thirty-one amino acids in length and has the following amino acid sequence:

Tyr—Cys—Gln—Lys—Trp—Met—Trp—Thr—Cys—Asp—Glu—
Glu—Arg—Lys—Cys—Cys—Glu—Gly—Leu—Val—Cys—Arg—
Leu—Trp—Cys—Lys—Lys—Lys—Ile—Glu—Trp (SEQ ID NO: 1)

The present invention also provides a method of treating arrhthymia, particularly cardiac arrhthymia comprising administering to a patient in need of such treatment an effective amount of the peptide.

The present invention additionally provides a method of mediating hypotonic cell swelling induced calcium increase (HICI) in cells comprising administering to a cell an effective amount of the peptide α mechanotoxin to block stretch activated channels.

The present invention further provides pharmaceutical compositions comprising the peptide and a pharmaceutically acceptable carrier or diluent.

In addition to the treatment of arrhthymia, the peptide of the invention can be used in biological assays as described herein.

DETAILED DESCRIPTION OF THE INVENTION

Applicants have discovered a novel peptide from venom of the Chilean pink tarantula spider, *Grammostola spatulata*. The novel purified peptide blocks stretch-activated channels in cell membranes and is thus useful in treating cardiac ventricular rhythm disturbances. The novel peptide of the invention is thirty-one amino acids in length and has the following amino acid sequence:

Tyr—Cys—Gln—Lys—Trp—Met—Trp—Thr—Cys—Asp—Glu—
Glu—Arg—Lys—Cys—Cys—Glu—Gly—Leu—Val—Cys—Arg—
Leu—Trp—Cys—Lys—Lys—Lys—Ile—Glu—Trp (SEQ ID NO: 1)

The peptide of the invention (referred to herein as α mechanotoxin or GsAF II) contains six cysteine residues and is not structurally similar to known peptides.

The present invention provides a method for treating cardiac arrhthymia comprising administering to a mammal in need of such treatment an effective amount of a peptide having the amino acid sequence Tyr—Cys—Gln—Lys—Trp—Met—Trp—Thr—Cys—Asp—Glu—
Glu—Arg—Lys—Cys—Cys—Glu—Gly—Leu—Val—Cys—Arg—
Leu—Trp—Cys—Lys—Lys—Lys—Ile—Glu—Trp (SEQ ID NO: 1)

The peptide α mechanotoxin is useful for treating cardiac arrhthymia in mammals, including man, conventional laboratory animals such as rats, mice and guinea pigs, and any other species of mammal.

Ventricular fibrillation is a frequent cause of sudden death. The cause of ventricular fibrillation has not been identified with certainty. Without wishing to be bound by any particular mechanism or theory of action, Applicants believe the peptide of the invention prevents or reverses cardiac arrhthymia by inhibiting or reducing ventricular fibrillation as a result of blocking stretch-activated channels present in the heart. It has been suggested that abnormal mechanical factors induce electrophysical changes conducive to arrhthymia via mechanoelectric feedback. Sarcolemmal stretch-activated channels in some cells have been postulated as a mechanism of mechanoelectric feedback and they appear to play a role in the initiation of stretch-activated arrhthymias. The peptide of the invention preferentially blocks stretch-activated channels and the hypotonic cell swelling induced calcium increase associated with the activation of such channels.

α Mechanotoxincan can be prepared for pharmaceutical use by incorporation with a pharmaceutically acceptable carrier or diluent. Thus, a further aspect of the present invention provides a pharmaceutical composition comprising α mechanotoxin and a pharmaceutically acceptable carrier or diluent. The peptide can be prepared for pharmaceutical use by incorporating it in unit dosage form as tablets or capsules for oral or parenteral administration either alone or in combination with suitable carriers such as calcium carbonate, starch, lactose, talc, magnesium stearate, and gum acacia. The peptide can be formulated for oral, parenteral or intravenous administration in aqueous solutions, aqueous alcohol, glycol or oil solutions or oil-water emulsions. These and other suitable forms for the pharmaceutical compositions of the invention can be found in *Remington's Pharmaceutical Science*, 15th ed., Mack Publishing Company, Easton, Pa. (1980). α Mechanotoxin can be administered orally, parenterally or intravenously, or by any other route.

The amount of the active component (i.e. peptide) in the pharmaceutical compositions can be varied so that a suitable dose providing an effective antiarrhythmic amount can be administered to a patient. The dosage administered to a particular patient will depend on a number of factors such as the route of administration, the duration of treatment, the size and physical condition of the patient, the potency of the peptide and the patient's response thereto. An effective antiarrhythmic amount of the peptide is generally in the range of from about ten micrograms per kilogram body weight of the patient to about one gram per kilogram; preferably from about 0.1 milligram per kilogram to about 100 milligrams per kilogram; more preferably from about one milligram per kilogram to about ten milligrams per kilogram. An effective antiarrhythmic amount can be estimated by testing the peptide in a guinea pig heart model that measures arrhthymia such as the model disclosed in Lab et al., Exp. Physiol. 79: 249–255, 1994 to arrive at a dose that can be varied according to one or more of the criteria listed above to provide a suitable amount of the peptide to the mammal.

As used herein, the term antiarrhythmic activity refers to the activity of the peptide of the invention of blocking stretch-activated channels, particularly those in the heart or other organ, or inhibiting cardiac arrhthymia in mammals including man. An antiarrhythmic effective amount refers to an amount of the peptide that blocks stretch-activated channels in the heart or other organ or inhibits cardiac arrhthymia.

In addition to its use in the treatment of arrhthymia, the peptide of the invention can also be used in biological assays, such as assays to evaluate the site of action of the peptide, assays to study the mechanism of action of the peptide and screening assays to discover other molecules that either block or mimic the action of the peptide on the stretch-activated channels.

For use as a reagent in such assays, the peptide preferably incorporates a detectable label, thus providing an additional embodiment of the invention. The detectable label can be any conventional type of label and is selected in accordance with the type of assay to be performed. For example, the detectable label can comprise a radiolabel such as $^{14}C$, $^{125}I$, or $^{3}H$, an enzyme such as peroxidase, alkaline or acid phosphatase, a fluorescent label such as fluoroisothiocyanate (FITC) or rhodamine, an antibody, an antigen, a small molecule such as biotin, a paramagnetic ion, a latex particle, an electron dense particle such as ferritin or a light scattering particle such as colloidal gold. Suitable methods to detect such labels include scintillation counting, autoradiography, fluorescence measurement, calorimetric measurement or light emission measurement. Suitable assays and procedures for accomplishing such labeling and detection of the labels are well known in the art and can be found, for example, in *An Introduction to Radioimmunoassays and Related Techniques: Laboratory Techniques in Biochemistry and Molecular Biology*, 4th Ed., T. Chard, Elsevier Science Publishers, Amsterdam, The Netherlands, 1990; *Methods in Non-Radioactive Detection*, Gary C. Howard, Ed., Appleton and Lange, East Norwalk, Ct., 1993 or *Radioisotopes in Biology*: A Practical Approach, R. J. Slater, Ed., IRL Press at Oxford University Press, Oxford, England, 1990.

For example, the peptide can be labeled with $^{125}I$ according to conventional methods known in the art and used to determine the location of stretch-activated channels in a tissue sample such as a sample of heart tissue, cell membrane preparations or isolated cells. The labeled peptide will bind to stretch-activated channels in the tissue, membrane preparation or cells and the presence of the $^{125,}$ label can be detected be scintillation counting or autoradiography, thus signaling the presence in the tissue, membrane preparation or cells of stretch-activated channels.

Methods of identifying compounds that mimic or block the antiarrhthymic activity of α mechanotoxin comprise adding a test compound to an assay that measures the effect of α mechanotoxin on stretch-activated channels and detecting the activity of the test compound. Suitable assays that measure the effects of α mechanotoxin on stretch activated channels include the fluorescence ratio measurement assay described herein in the examples. Suitable test compounds include small organic molecules, antibodies, peptides and proteins. Compounds that mimic the effect of α mechanotoxin will have the same or similar type of activity as α mechanotoxin and can be used in the same way. Compounds that block the effect of α mechanotoxin can be used as inhibitors of the peptide.

A further aspect of the invention provides a method of mediating hypotonically induced calcium increase in swollen cells comprising administering to a cell a stretch activated channel blocking effective amount of the peptide a mechanotoxin. The method of this aspect of the invention can be used to inhibit hypotonic swelling induced calcium increase in any type of cells wherein stretch-activated channels are present including heart, pituitary and muscle cells, neurons and glial cells.

A stretch-activated channel blocking effective amount refers to an amount of α mechanotoxin effective to block stretch-activated channels in any type of mammalian cell. An effective amount preferably ranges from about 10 nanomoles to about 1 millimole, preferably from about 0.1 micromole to about 100 micromoles, more preferably from about one micromole to about 10 micromoles. An effective amount can be determined using the assay described herein in the Examples or any other stretch-activated channel assay that measures the activity of the channels.

The present invention also provides antibodies specific for α mechanotoxin. The term antibody as used herein includes all immunoglobulins and fragments thereof which contain recognition sites for antigenic determinants of the peptide of the present invention. The antibodies of the present invention may be polyclonal or preferably monoclonal, may be intact antibody molecules or fragments containing the active binding region of the antibody, e.g. Fab or $F(ab)_2$ and can be produced using techniques well established in the art. Such antibodies can then be used, for example, to locate α mechanotoxin bound to stretch-activated cells in tissue containing cells that express such channels.

α Mechanotoxin can be prepared by purification or isolation from *Grammostola spatulata* venom, chemical synthesis or recombinant DNA methods. *Grammostola spatulata* venom is commercially available from Spider Pharm, Feasterville, Pa., U.S.A. The peptide can also be obtained by methods known in the art such as electrical stimulation of the spider to cause release of the venom followed by collection of the venom by suction or other method. The peptide is preferably isolated from spider venom by sequential fractionation using reverse phase-high pressure liquid chromatography on C-8 and C-18 silica supports with trifluoroacetic acid/acetonitrile buffer. A preferred C-8 silica support is Zorbax® Rx C-8 (Mac-Mod Analytical, Inc., West Chester, Pa. which is comprised of 5 micron diameter silica particles having 300 Å pore size and covalently modified to contain diisopropyloctyl side chains. The C-18 silica support is preferably comprised of 5 micron diameter silica particles having 300 Å pore size and covalently modified to contain an octadecyl side chain. Other types of C-8 and C-18 silica supports are also suitable for use in isolating the peptides. A preferred buffer is 0. 1% trifluoroacetic acid in acetonitrile.

Peptide α mechanotoxin can also be prepared by chemical synthesis using either automated or manual solid phase synthetic technologies. Such technologies are well known in the art and can be found, for example, in E. Atherton and R. C. Sheppard, Solid Phase Peptide Synthesis: A Practical Approach, IRL Press/Oxford University Press, Oxford, England, 1989, or M. Bodanszky, Peptide Chemistry: A Practical Textbook, Springer-Verlag, New York, N.Y., 1988.

For example, the peptide can be synthesized using Fmoc chemistry or an automated synthesizer. Dependent on quantitative yields, production of the linear reduced peptide can be performed in either a single process or in two different processes followed by a condensation reaction to join the fragments. A variety of protecting groups can be incorporated into the synthesis of linear peptide so as to facilitate isolation, purification and/or yield of the desired peptide. Protection of cysteine residues found in the peptide can be accomplished using, for example, a triphenylmethyl, acetamidomethyl and/or 4-methoxybenzyl group in any combination. Such a strategy may offer advantages for subsequent oxidation studies to yield folded peptide.

Additionally, peptide α mechanotoxin can be prepared by recombinant DNA techniques. A DNA sequence coding for the peptide is prepared, inserted into an expression vector and expressed in an appropriate host cell. The peptide is then purified from the host cells and/or cell culture medium. Methods for preparing DNA coding for the peptide and expression of the DNA are well-known and can be found, for example, in Sambrook et al. (1989) *Molecular Cloning: A Laboratory Manual*, Cold Spring Harbor, N.Y.: Cold Spring Harbor Laboratory Press, Cold Spring Harbor, N.Y.; S. L. Berger and A. R. Kimmel, Eds., *Guide to Molecular Cloning Techniques: Methods in Enzymology, vol.*152, Academic Press, San Diego, Cal., 1987 and in E. J. Murray, Ed. *Gene Transfer and Expression Protocols: Methods in Molecular Biology*, vol.7, Humana Press, Clifton, N.J., 1991.

As used herein, a purified or isolated peptide refers to a peptide that is substantially free of contaminating cellular components, other venom constituents or other material. Preferably, the peptide is present in a mixture containing the peptide in an amount greater than about 50% of the total mixture, more preferably in an amount greater than about 80%, most preferably in an amount greater than about 90%.

EXAMPLES

Example 1

Isolation of peptide α Mechanotoxin Isolation and Characterization of Peptide a Mechanotoxin A. Isolation of Peptide Crude *Grammostola spatulata* venom was supplied, as frozen aliquots, by the commercial vendor Spider Pharm, Inc. (Feasterville, Pa. 19053). Reverse phase-high pressure liquid chromatography (RP-HPLC) of the venom was performed using Zorbax® Rx-C8 semi-preparative (25 cm×9.4 mm) and analytical (25 cm×4.6 mm) columns (Mac-Mod Analytical, Inc. West Chester, PA; Zorbax® Rx-C8 is comprised of 5 micron silica microsphere particles having a 300Å pore size and covalently modified with diisopropyl octyl side chains) and a C-18 analytical (25 cm×4.6 mm) column (Vydac, Hesperia, Calif.; the C-18 support is comprised of 5 micron silica microsphere particles having a 300Å pore size and covalently modified with octadecyl side chains). Semi-preparative scale RP-HPLC was done using a 5 milliliter/minute flow rate whereas a 1 milliliter per minute flow rate was used for the analytical analyses.

Detection of eluting entities was monitored via ultraviolet (UV) spectroscopy at 215 nm and fractions were either collected at 1 minute intervals or manually based upon UV intensity. Initial injection volumes of 30–50 microliter (ml) crude venom were made. Consequently, multiple fractionations were carried out at each stage of the purification with pooling of individually identical fractions. All fractions were lyophilized prior to resuspension in HPLC grade $H_2O$ for subsequent purification or testing. Resuspension volumes were based upon original crude venom volumes. Evaluation was done on samples deemed to be greater than 90% homogeneous by RP-HPLC. Samples were stored at 4° C. following resuspension. No detectable loss of activity was witnessed with storage or with adherence to either plastic or glass.

Initial fractionation of crude *Grammostola spatulata* venom on the Zorbax® RX-C8 semi-preparative column was done with a 20–50% gradient of $TFA/CH_3CN$ Buffer (0.1% trifluoroacetic acid in acetonitrile) over 30 min with a 3 minute delay. ($TFAICH_3CN$ Buffer was prepared by adding 4 ml of trifluoroacetic acid to 4 liters of acetonitrile). Column flow rate was 5 milliliters per minute and fractions collected at one minute intervals. Fraction 19 was highly enriched for. Following lyophilization and resuspension of fraction 19, further separations of this fraction were performed with shallower gradients of $TFA/CH_3CN$ Buffer.

Fraction 19 was applied to a Zorbax® RX-C8 semi-preparative column and fractionated using either a 29–33% or a 30–34% gradient of $TFA/CH_3CN$ Buffer over 24 minutes with a 3 minute delay. The major UV absorbing peak was manually collected with removal of peak tails. After this step, sample purity was usually found to be at least 85%. The major UV absorbing peak was further purified using a 20–50% gradient of $TFA/CH_3CN$ Buffer over 30 min with a 3 minute delay. The primary peak which elutes at 23.5 minutes was collected manually with removal of peak tails. α Mechanotoxin sample purity was found to be about 95% pure.

B. Characterization of Peptide

1. Electrospray Mass Spectrometry (ES-MS) Analysis of Molecular Weight and Disulfide Bridge Assignment:

Electrospray spectra were acquired for the peptide using a mass spectrometer (VG/Fisons QUATTRO, Fisons Instruments, Inc. Manchester, UK) in the continuum acquisition mode. The $(M+3H)^{3+}$, $(M+4H)^{4+}$ and $(M+5H)^{5+}$ charge states were observed for each sample and mathematically transformed to yield a zero charge state spectrum. Analyses were performed on both the native/oxidized and the reduced state of the peptide. Lyophilized was reduced in 0.5M dithiothreitol (DTT), 0.11M N-ethylmorpholine, pH 8.5, at 38C for 10 min. Flow injections containing approximately 200–400 picomoles of peptide were measured. The average molecular weight of was determined to be 3979.9 Daltons (Da). After thiol reduction, the average molecular weight was measured at 3985.9 Daltons. Since each reduction of a disulfide bond increases the mass of a peptide by 2 Da, the peptides contain three disulfide linkages based upon the 6 Da mass shift.

2. Amino Acid Analysis:

Amino acid composition analyses were performed using an amino acid analyzer (Applied Biosystems 420H, Foster City, Calif.). Data normalization was done with respect to leucine. No discrepancies (excluding those residues which are either partially or totally destroyed during hydrolysis) in residue/mol values were recorded with respect to the Edman N-terminal sequencing analysis.

Amino acid composition analysis yielded the data presented in the table below. Since tryptophan is completely destroyed and cysteine is partially destroyed in this analysis, their presence was inferred from UV spectroscopy and electrospray mass spectral analysis, respectively. Residue/mol values were calculated on the basis of using Leu as the standard.

| Residue | Total Amount (pmole) | Residue/mol |
|---|---|---|
| Asp/Asn | 701.2 | 1.2 |
| Glu/Gln | 2767.6 | 4.7 |
| Gly | 618.1 | 1.0 |
| His | 0 | — |
| Arg | 1050.0 | 1.8 |
| Thr | 518.9 | 0.9 |
| Ala | 35.5 | 0.1 |
| Pro | 36.7 | 0.1 |
| Tyr | 547.5 | 0.9 |
| Val | 523.9 | 0.9 |
| Met | 875.7 | 1.5 |
| Cys | 2124.1 | 3.6 |
| Ile | 545.3 | 0.9 |
| Leu | 1186.1 | 2.0 |
| Phe | 48.5 | 0.1 |
| Lys | 2639.7 | 4.5 |

3. N-terminal Sequence Analysis of Reduced, Pyridylethylated Peptides and or Proteolytically Digested Fragments:

N-terminal sequencing was performed on a gas phase sequencer (Applied Biosystems 475, Foster City, Calif.). SDS-Page was performed using a 16.5% high cross linked Tris-Tricine gel according to the method of Schagger, H. and G. von Jagow, Anal. Biochem. 166: 368–379, 1987, and electroblotted to ProBlot (Applied Biosystems) as described by Matsuidara et al , J. Biol. Chem. 262:10035–10038. Electroblotted bands were pyridylethylated in the gas phase according to the method described in Andrews, P. C. and J. E. Dixon, Anal. Biochem. 161: 524–528, 1987. Covalent attachment of peptides via activation of carboxyl groups and reaction with arylamine derivatized polyvinylidene difluoride (PVDF) using sequalon membranes (Millipore Inc., Milford, Mass.) was performed according to the manufacturer's instructions. V8 proteolytic digestion of reduced [100 ×dithiothreitol (DTT) vs. Cys] α mechanotoxin peptide was done in 50 mM Na phosphate buffer, pH 7.8, for 18 hr. using an enzyme:substrate ratio of 1:44. Fragments were isolated using RP-HPLC and their mass analyzed using laser desorption/ionization mass spectrometry prior to sequence analysis. Samples were applied to the sequencer either as direct solutions onto a coated disc or as covalent coupled entities to ascertain carboxyl terminal acidification/amidation. Shown below is the sequence obtained for α mechanotoxin:

Tyr—Cys—Gln—Lys—Trp—Met—Trp—Thr—Cys—Asp—Glu—Glu—Arg—Lys—Cys—Cys—Glu—Gly—Leu—Val—Cys—Arg—Leu—Trp—Cys—Lys—Lys—Lys—Ile—Glu—Trp (SEQ ID NO: 1)

Deduction of the Trp-3 1 of α mechanotoxin is based upon amino acid compositional data in conjunction with the ES-MS. Specifically the unaccounted mass difference between the calculated mass value for the Edman deduced sequence and the mass spectral analysis for the native peptide is 186 Da. This mass differential (+or −1 Da) could be accounted for by multiple amino acid combinations. However, upon review of the amino acid compositional data, none of those combinations are in good agreement. Since the mass of an internal Trp is 186 Da, and the Trp is destroyed under the hydrolysis conditions, assignment of Trp to position 31 as a free acid has been made.

4. UV Spectroscopy:

A complete spectrum was obtained for α mechanotoxin using a 8452A diode array spectrophotometer (Hewlett Packard, Avondale, Pa., USA). Concentration of the final peptide was deduced from the $Abs_{280nm}$. Based upon the differential contributions from 4 Trp, 1 Tyr and slight contribution from 6 Cys, the calculated molar extinction coefficient of α mechanotoxin was deduced to be 24310. Using this value, UV spectroscopy analyses of native α mechanotoxin preparations indicate that the venom concentration of this peptide is approximately 3–5 mM.

Example 2

Fluorescence ratio measurement of stretch activated channel activity

A. $GH_3$ Cell culture

Rat pituitary cell line $GH_3$ was provided by Dr. S. Simasko, Department of VCAPP, Washington State University, Pullman, Wash., 99164 and the American Type Culture Collection, Rockville, Md. The cells were cultured in standard medium containing 82.5% Ham's F-10 nutrients (Gibco, Gaithersburg, Md.), 15 % heat inhibited horse serum (Gibco) and 2.5% fetal bovine serum (Gibco) at 37C in 10% $CO_2$. Cells were fed twice per week and subcultured once per week. For Fura-2 fluorescence measurements, cells were plated on poly-L-lysine coated glass cover slips at 95% confluency, cultured under normal conditions and used between 3 to 6 days after plating.

B. Fura-2 Fluorescence ratio measurement of $Ca^{2+}$ $Ca^{2+}$ was measured on an SLM AB-2 fluorescence spectrometer (SLM Instruments, Rochester, N.Y.). Cells plated on poly-L-lysine coated glass cover slips were loaded with Fura-2 in a loading solution containing 2 micromolar Fura-2/AM (disclosed in Grynkiewicz, G. et al., (1985) Journal of Biological Chemistry 260: 3440–3450) according to the following procedure. Cells were washed twice in phosphate buffered saline (PBS) solution. Cells were then incubated in the loading solution for 30 minutes at 25C. The cells were rinsed twice with PBS and incubated in the culture medium for 30 minutes at 25C. Experiments were performed within 1 hour after loading.

Composition of the Fura-2 loading solution is as follows: normal saline plus 2 mM Fura-2/AM and 0.05% Pluronic-F127 detergent (BASF, Wyandotte).

After loading, the plated cells were exposed to various hypotonic and isotonic solutions and test solutions containing spider venom. Changes in the calcium ion concentration were measured according to the following method.

After loading with Fura-2, the cover slip containing the $GH_3$ cells was mounted in a custom made holder and placed in a quartz cuvette at an angle of 20 degrees to the excitation beam. The cells on the cover slip were exposed to various test solutions and the changes in calcium ion concentration were measured according to the following method. Fluorescence emission was collected from a group of about $10^5$ cells located in the excitation path. Excitation beams at 340 nm (Ex340 nm) and 380 nm (Ex380nm) were used and the fluorescence intensities at 510 nm (Em510 nM) were monitored. The maximum data acquisition rate was two data points per second. Fluorescence emission data was collected for times up to 600 to 1200 seconds depending on the solution added to the cells.

An increase in the $Ca^{2+}$ concentration caused an increase in the fluorescence at Em510 nm/Ex340nm and at the same time, a decrease at Em510/Ex380nm. The ratio of the two (R) was used to calculate the $Ca^{2+}$ concentration using the following formula:

$$[Ca^{2+}] = k_d \cdot \frac{R - R_{min}}{R_{max} - R} \cdot \frac{F_f}{F_b}$$

where kd is the equilibrium constant; $R_{max}$ is the ratio and $F_b$ is the fluorescence intensity at Ex380 nm when Fura-2 is saturated with $Ca^{2+}$, $R_{min}$ is the ratio and $F_f$ is the fluorescence intensity at Ex380nm when Fura-2 is not bound by $Ca^{2+}$. $R_{max}$ and $F_b$ were obtained by using the $R_{max}$ solution containing 5 mM $Ca^{2+}$ to saturate Fura-2. $R_{min}$ and $F_f$ were then obtained by using the $R_{min}$ solution containing SmM EGTA to chelate the remaining $Ca^{2+}$. $k_d$=224 nM was used for the high $K^+$ condition, as given by Grynkiewic et al., J. Biol. Chem 260: 3440–3450, 1985.

*Grammostola spatulata* venom was purchased from Spider Pharm (Feasterville, Pa.).

The only difference between the isotonic and hypotonic solutions were the mannitol concentration so that the concentration of all the ions was kept constant. A six line perfusion system was used to change solutions. A complete change of solutions took 1 minute or less depending on the chamber volume. To avoid mechanical disturbances, solution flow was kept constant throughout the experiments.

Composition of $R_{max}$ solution: 20 mM sodium chloride, 115 mM potassium chloride, 5 mM calcium chloride, 1 mM magnesium chloride, 10 mM 4-(2-hydroxyethyl)-1-piperazineethanesulfonic acid (HEPES), 20 mM mannitol, 0.10% polyethylene glycol tert-octylphenyl ether (Triton X-100 Sigma Chemical Co., St. Louis, Mo.) in water; osmolarity of the solution is 318 milliosmoles Composition of $R_{min}$ solution: 20 mM sodium chloride, 115 mM potassium chloride, 1 mM magnesium chloride, 10 mM HEPES, 30 mM mannitol, 5 mM ethylenebis (oxyethylenenitrilo) tetraacetic acid (EGTA), 0.10% Triton in water; osmolarity of the solution is 318.

C.1 Hypotonic swelling caused a significant increase of $Ca^{2+}$

Exposing $GH_3$ cells to the normal hypotonic solution caused a significant increase of $Ca^{2+}$+. Cells had a basal level $Ca^{2+}$ of approximately 30 nM in the isotonic solution. Switching to the hypotonic solution caused $Ca^{2+}$ to increase to approximately 250 nM. Returning to isotonic solution caused $Ca^{2+}$ to rapidly decrease to the basal level.

Composition of the isotonic solution: 65 mM sodium chloride, 5 mM potassium chloride, 1 mM calcium chloride, 2 mM magnesium chloride, 10 mM HEPES, and 160 mM mannitol in water; osmolarity of the solution is 319.

Composition of the hypotonic solution: 65 mM sodium chloride, 5 mM potassium chloride, 1 mM calcium chloride, 2 mM magnesium chloride, 10 mM HEPES, and 20 mM mannitol in water; osmolarity of the solution is 179.

The hypotonic cell swelling induced calcium increase (HICI) response in $GH_3$ cells consistently showed four characteristics: 1) switching to normal hypotonic solution caused a significant increase of $Ca^{2+}$. The magnitude of the $Ca^{2+}$ increase varied among experimental cell groups, perhaps due to the variations in the cells culture conditions. Nevertheless, the peak $Ca^{2+}$ increase ranged from 4–11 times the basal level. 2) The onset of the $Ca^{2+}$ increase had a delay time ranging from 50 seconds to 4 minutes, with an average of 1.5 minutes. 3) $Ca^{2+}$ remained elevated during the entire period of hypotonic exposure. The longest time tested was 12 minutes. 4) Returning to isotonic solution caused $Ca^{2+}$ to return to the basal level within 30 seconds.

C.2 Extracellular $Ca^{2+}$ was necessary for HICI The dependence of HICI on extracellular $Ca^{2+}$ was studied by removing $Ca^{2+}$ from the hypotonic solution as three different stages of exposure. In the first experiment, $Ca^{2+}$ was removed form the hypotonic solution simultaneously with hypotonic exposure. $Ca^{2+}$+ remained at the basal level of 50 nM, showing that HICI was abolished in the absence of extracellular $Ca^{2+}$+. Return to the isotonic solution (which contains 1 mM $Ca^{2+}$) caused $Ca^{2+}$ to decline to the basal level within 30 seconds. With large volume chambers that exhibited slow exchange, there was often a transient increase in intracellular $Ca^{2+}$ following return to normal saline. This was caused by the influx of reintroduced $Ca^{2+}$ flowing through stretch activated channels before cell shrinkage turned them off. In the second experiment, $Ca^{2+}$ was removed from the hypotonic solution after $Ca^{2+}$ had been elevated during HICI. In this experiment, a normal hypotonic exposure caused $Ca^{2+}$ to increase from a basal level of 30 nM to a plateau level of 160 nnM. $Ca^{2+}$ was then removed from the hypotonic solution, resulting in a rapid decrease of $Ca^{2+}$ to the basal level. Thus, a continued presence of extracellular $Ca^{2+}$ was necessary for HICI.

In the third experiment, cells were first exposed to $